United States Patent [19]

Yokota et al.

[11] Patent Number: 5,552,116
[45] Date of Patent: Sep. 3, 1996

[54] TEST STRIP PICK-UP MECHANISM IN AUTOMATED ANALYZER

[75] Inventors: Hiroshi Yokota; Keiji Takahashi, both of Hiratsuka, Japan

[73] Assignee: Bayer Corporation, Elkhart, Ind.

[21] Appl. No.: 423,322

[22] Filed: Apr. 17, 1995

[30] Foreign Application Priority Data

May 10, 1994 [JP] Japan ................................. 6-119687

[51] Int. Cl.⁶ ............................................. G01N 35/00
[52] U.S. Cl. .............................. 422/63; 422/66; 422/99; 436/43; 436/46
[58] Field of Search ................................. 422/63, 66, 99, 422/104; 436/43, 46, 174, 807, 810

[56] References Cited

U.S. PATENT DOCUMENTS

| | | | |
|---|---|---|---|
| 4,279,514 | 7/1981 | Blümel et al. | 356/445 |
| 4,876,204 | 10/1989 | Inoue et al. | 436/46 |
| 5,298,425 | 3/1994 | Kuhn et al. | 436/43 |
| 5,415,840 | 5/1995 | Sano et al. | 422/67 |
| 5,447,690 | 9/1995 | Sugaya | 422/64 |

Primary Examiner—James C. Housel
Assistant Examiner—Long V. Le
Attorney, Agent, or Firm—Roger N. Coe

[57] ABSTRACT

A test strip pick-up mechanism in an automated analyzer, which comprises: a bottle holder removably holding a test strip bottle containing a plurality of test strips and having a pierced groove formed in the peripheral direction and a test strip pick-up portion connected to the groove and formed in the longitudinal direction; a bottle turning motor connected to the bottle holder; a guide member extended from the inner part of the bottle holder in parallel to the central axis of the test strip bottle and having a L-shaped guide portion formed over the entire length of the guide member with suction holes for adsorbing the test strips being formed on the guide portion which is adjacent to the test strip pick-up portion; claws engaged with the groove of the bottle holder; an air chuck having suction holes for drawing out the test strips contained in the test strip bottle; a movable member on which the air chuck is mounted; a test strip drawing out motor connected to the movable member via a guide bar; depressing arms for pushing the air chuck downward; and an air chuck depressing motor connected to the depressing arms via a shaft.

2 Claims, 6 Drawing Sheets

5,552,116

TEST STRIP PICK-UP MECHANISM IN AUTOMATED ANALYZER

BACKGROUND OF THE INVENTION

This invention relates to a test strip pick-up mechanism in an automated analyzer, more specifically to a test strip pick-up mechanism in an automated analyzer by which test strips can automatically be supplied smoothly and, for example, when a test strip bottle (i.e., a test strip container) containing a plurality of commercially available test strips is set as such in an analyzer, the test strips can directly be picked up from the test strip bottle without providing any specially designed test strips for the analyzer.

In the prior art, a test strip has been frequently used for testing a plurality of analysis items of a specimen such as urine easily and simply. As shown in FIG. 13, in a test strip 1, a plurality of test pads 3 impregnated with reagents are pasted on one end portion of a long and slender strip 2 made of plastic, and the other end portion is a holding portion 4. The respective specimen components are analyzed by dipping the test strip 1 in a specimen to wet the test pads 3 and measuring coloration intensities of the test pads 3 by an analyzer.

As an analyzer which handles the above test strips automatically, there may be mentioned an analyzer described in Japanese Provisional Patent Publication No. 91571/1986 (JP-A- 61-91571). This automated analyzer uses a slide base system in which a test strip is charged into a hopper and the bottom of the hopper is slid to transport the test strip outside the hopper. When the test strip is transported outside the hopper, the test strip is easily caught between the wall and the bottom of the hopper, whereby smooth operations are interrupted. Further, it is required to carry out operations of picking up the test strip from a test strip bottle containing a plurality of test strips and charging it into the hopper.

SUMMARY OF THE INVENTION

An object of the present invention is to provide a test strip pick-up mechanism in an automated analyzer, by which test strips can automatically be supplied smoothly one by one and, for example, when a test strip bottle containing a plurality of commercially available test strips is set as such in an analyzer, the test strips can directly be picked up from the test strip bottle without providing any specially designed test strips for the analyzer.

As shown in FIG. 1 to FIG. 8, the test strip pick-up mechanism in an automated analyzer of the present invention comprises:

a bottle holder 14 removably holding a test strip bottle 10 containing a plurality of test strips (not shown) and having a pierced groove 19 formed in the peripheral direction and a test strip pick-up portion 25 connected to the groove 19 and formed in the longitudinal direction;

a bottle turning motor 32 connected to the bottle holder 14;

a guide member 23 extended from the inner part 22 of the bottle holder 14 parallel to the central axis of the test strip bottle 10 and having a L-shaped guide portion 24 formed over the entire length of the guide member 23 with suction holes 26 for adsorbing the test strips being formed on the guide portion 24 which is adjacent to the test strip pick-up portion 25;

claws 21 engaged with the groove 19 of the bottle holder 14;

an air chuck 28 having suction holes 37 for drawing out the test strips contained in the test strip bottle 10;

a movable member 39 on which the air chuck 28 is mounted;

a test strip drawing out motor 41 connected to the movable member 39 via a guide bar 40;

depressing arms 42 for pushing the air chuck 28 downward; and an air chuck depressing motor 43 connected to the depressing arms 42 via a shaft 44.

As shown in FIG. 9 to FIG. 12, another test strip pick-up mechanism in an automated analyzer of the present invention comprises:

a bottle holder 50 removably holding a test strip bottle 10 containing a plurality of test strips (not shown);

a bottle turning motor 58 connected to the bottle holder 50;

an O-ring 63 mounted on the entire peripheral portion of the bottom of the bottle holder 50;

a turning auxiliary plate 64 which is contacted with the O-ring 63 and makes the bottle holder 50 turn on its axis;

an air chuck 67 having suction holes 69 for drawing out the test strips contained in the test strip bottle 10;

a movable member 76 on which the air chuck 67 is mounted such that the air chuck 67 is movable upward and downward;

a test strip drawing out motor 84 connected to the movable member 76 via a guide bar 79;

an air chuck depressing motor 80 connected to the air chuck 67 via a shaft 83;

flappers 78 disposed at the both sides of the test strip adsorbing portion of the air chuck 67, which open and close accompanied with upward and downward movements of the air chuck 67; and a receiving plate 65 having a curved surface and a linear member 66 both of which are provided at the positions left from a region where an opening 12 is moved by turning the test strip bottle 10.

BRIEF DESCRIPTION OF THE DRAWINGS

FIG. 7 is a back view of a main portion of the mechanism of

DESCRIPTION OF THE PREFERRED EMBODIMENTS

Figure 1:
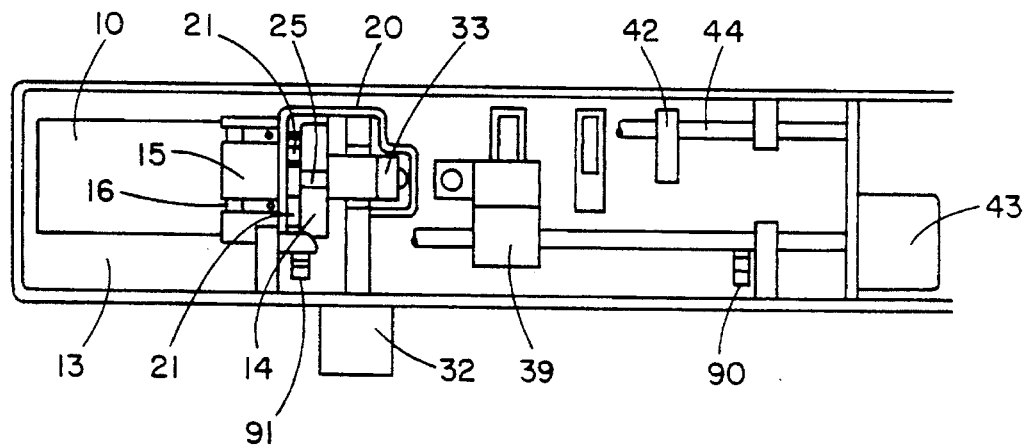
FIG. 1 is a plane view of one embodiment of the test strip pick-up mechanism of the present invention.
Figure 2:
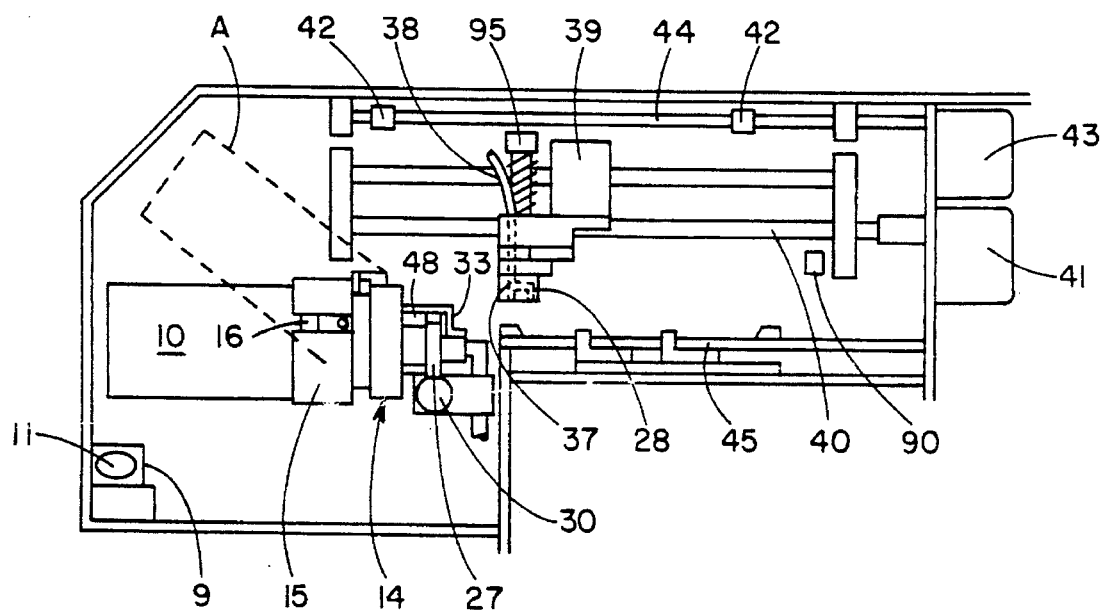
FIG. 2 is a side view of the mechanism of FIG. 1.
Figure 3:
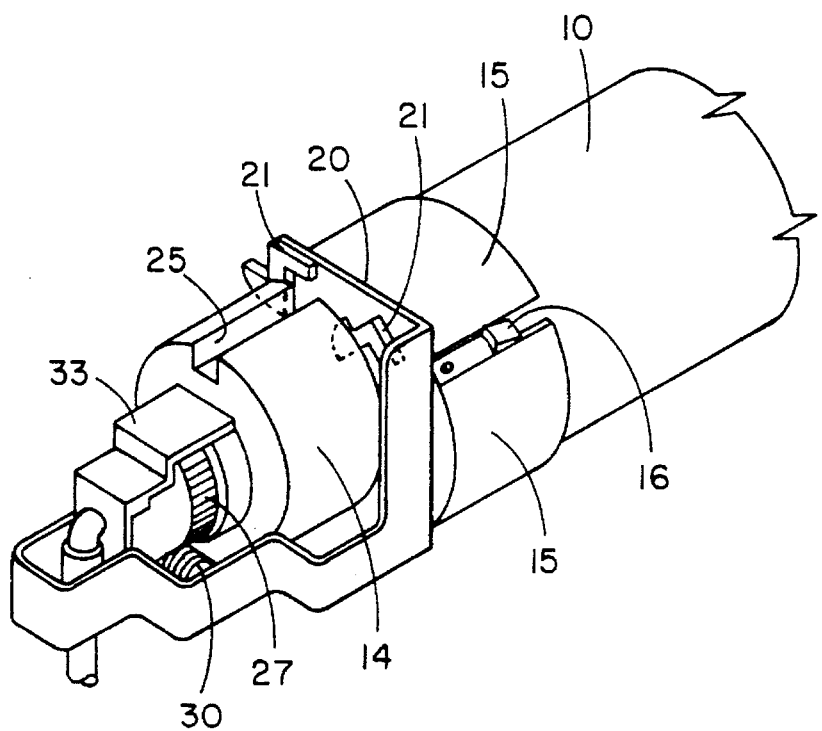
FIG. 3 is a perspective view of a main portion of the mechanism of FIG. 1.
Figure 4:
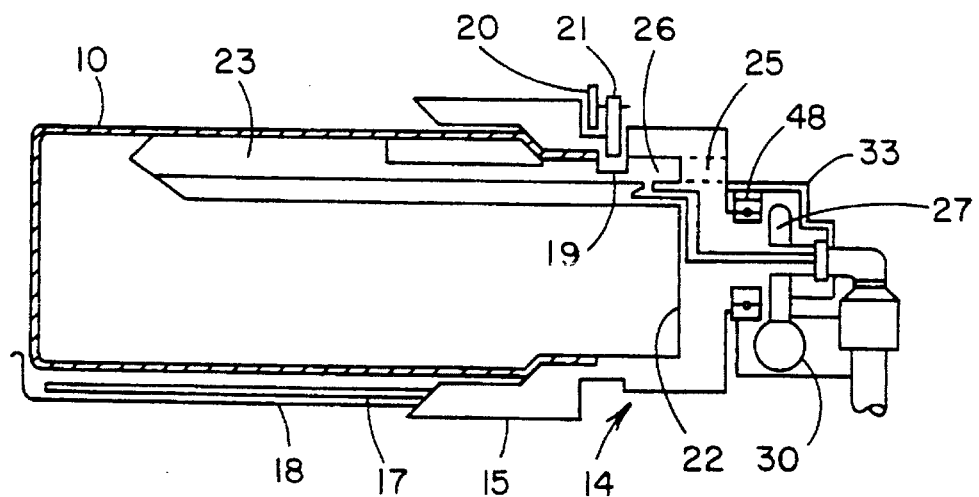
FIG. 4 is a sectional view of a main portion of the mechanism of FIG. 1.
Figure 5:
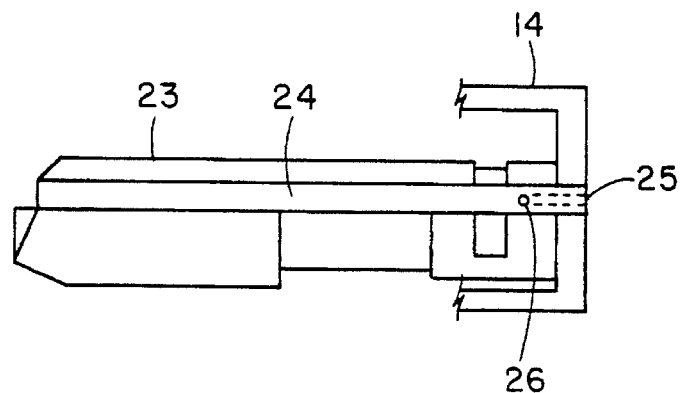
FIG. 5 is a plane view of a guide member of the mechanism of FIG. 1.
Figure 6:
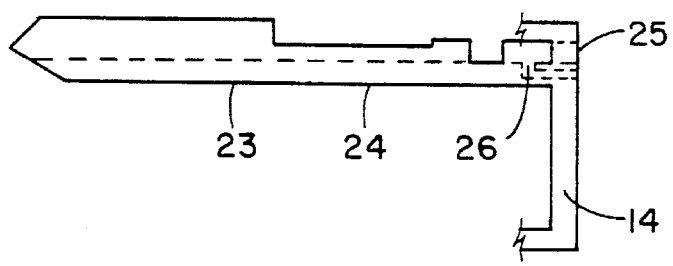
FIG. 6 is a side view of the guide member of FIG. 5.
Figure 7:
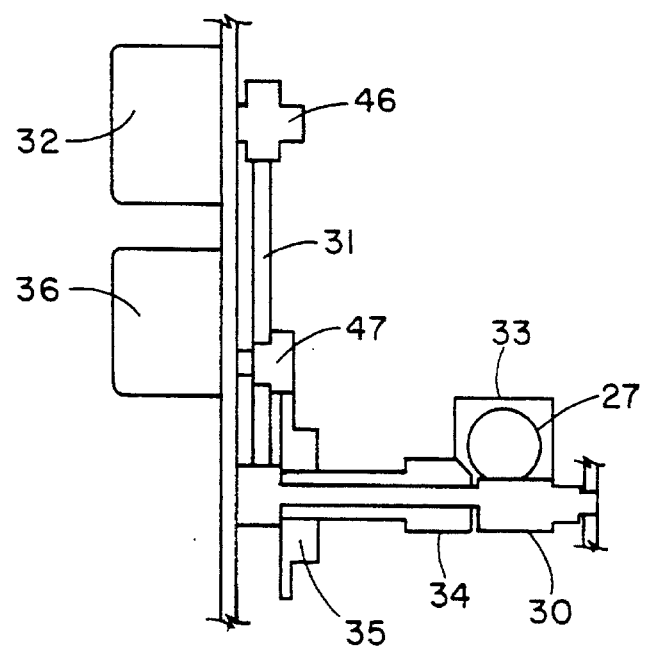
Figure 8:
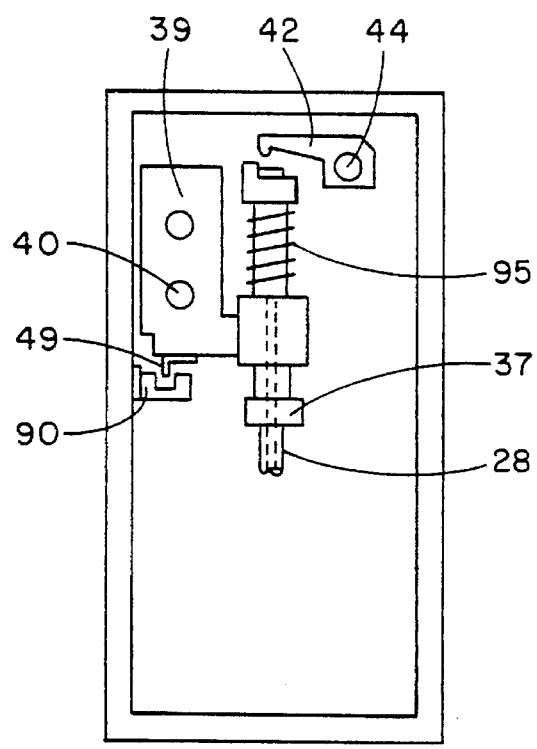
FIG. 8 is a front view of a main portion of the mechanism of FIG. 1.
Figure 9:
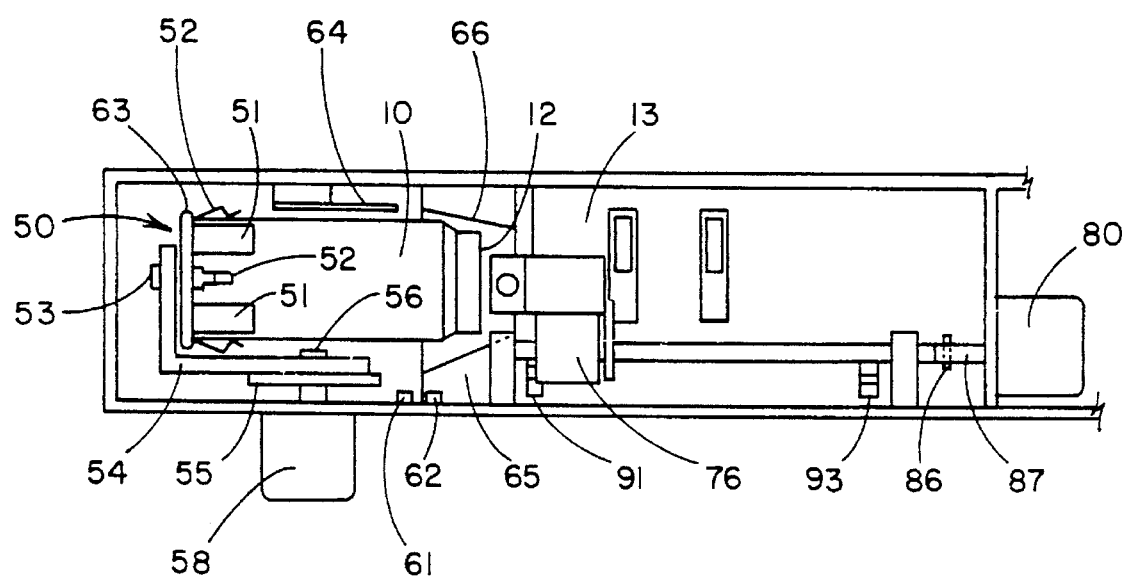
FIG. 9 is a plane view of another embodiment of the test strip pick-up mechanism of the present invention.
Figures 10, 11:
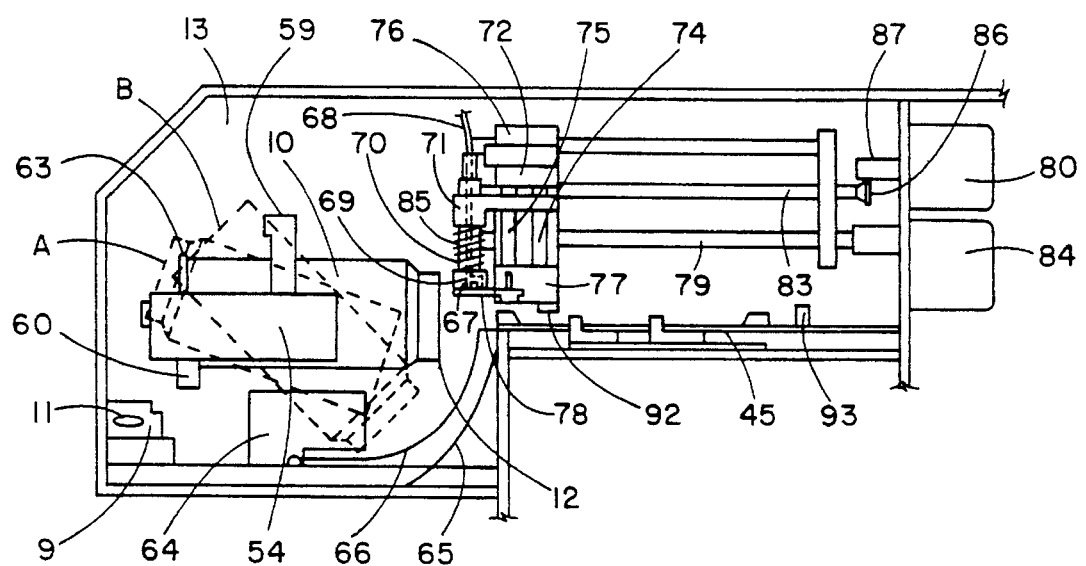
FIG. 10 is a side view of the mechanism of FIG. 9.
FIG. 11 is a perspective view of a main portion of the mechanism of FIG. 9.
Figure 12:
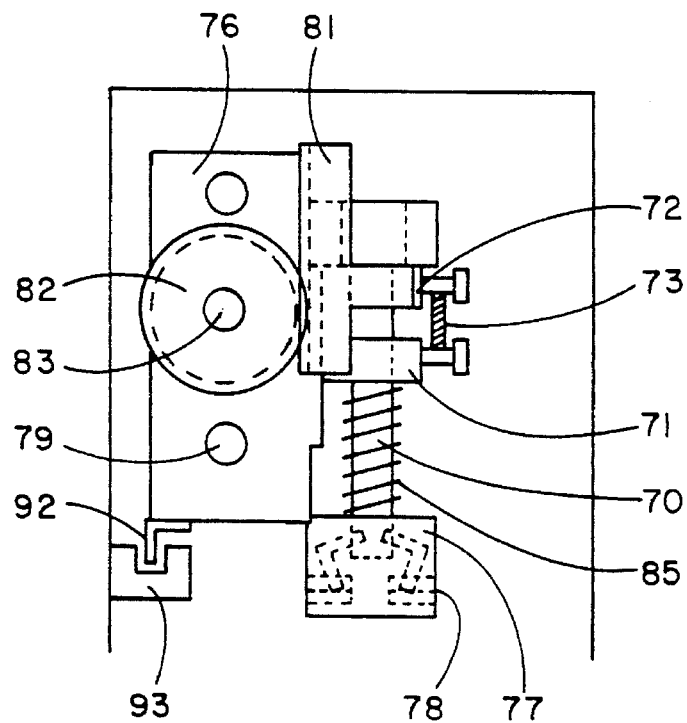
FIG. 12 is a front view of a main portion of the mechanism of FIG. 9.

In the following, the present invention is explained in detail.

In the test strip pick-up mechanism of the present invention, the test strip bottle 10 containing a plurality of the test strips 1 can be set as such in an analyzer, and the test strips 1 can directly be picked up from the test strip bottle 10. Also, a desiccant 11 can be used for desiccation in an airtight chamber 13. The test strip bottle 10 is formed such that its depth is slightly longer than the length of the test strips 1 and its diameter is smaller than the length of the test strips 1. Thus, even if the test strip bottle 10 containing the test strips 1 is turned so as to face the holding portions 4 to the opening 12, the test strips 1 are not stirred and moved in the test strip bottle 10 randomly, and the test pads 3 of the test strips 1 do not face to the opening 12.

In the case of the test strip pick-up mechanism shown in FIG. 1 to FIG. 8, the test strip bottle 10 is not engaged to the inner part 22 of the bottle holder 14, but engaged to about a half position thereof. After the test strip bottle 10 is engaged, it is once lifted up to Position A in FIG. 2, and the bottom thereof is usually lifted up about 5 to 10° from a horizontal plane. Thus, by engaging the test strip bottle 10 with the bottle holder 14, only the holding portions 4 of the test strips 1 protrude from the opening to reach the inner part 22.

When the test strip bottle 10 is reciprocatively turned on its axis, the test strips 1 are moved in the direction substantially orthogonal to its longitudinal direction, and the test strips 1 are slid into the guide portion 24 of the guide member 23. The claws 21 mounted on a frame 20 such that they are movable on the axis enter into the groove 19 by reciprocatively turning the bottle holder 14 on its axis, push the test strips 1 into the guide portion 24 and scrape out excess test strips 1 in the guide portion 24.

Discrimination whether the test strip 1 is adsorbed to the guide portion 24 or not is made by measuring a vacuum degree of air sucked from the suction holes 26 provided on the guide portion 24. That is, when the test strip 1 is adsorbed to the guide portion 24, the vacuum degree is increased, and on the other hand, when the test strip 1 is not adsorbed, the vacuum degree is not increased, whereby the discrimination can easily be made.

The test strip 1 slid into the guide portion 24 is adsorbed to the suction holes 26, so that the test strip 1 does not slip off the guide portion 24 even by reciprocatively turning the test strip bottle 10 on its axis. Even when two or more plural test strips are slid into the guide portion 24, only one test strip 1 is adsorbed to the suction holes 26.

By pushing one test strip 1 into the guide portion 24 and scraping excess test strips 1 by the claws 21 and reciprocatively turning the test strip bottle 10 on its axis, the excess test strips 1 slip off and only one test strip 1 is adsorbed to the guide portion 24. Thus, the test strips 1 can be drawn out one by one from the test strip bottle 10.

The test strip 1 obliquely adsorbed to the guide portion 24 is passed through the test strip pick-up portion 25 to be aligned in parallel to the air chuck 28. When the test strip 1 is not adsorbed to the guide portion 24, the test strip 1 is slid into the guide portion 24 by repeating reciprocative turning of the test strip bottle 10 on its axis, whereby the test strip 1 can securely be drawn out.

In the case of the test strip pick-up mechanism shown in FIG. 9 to FIG. 12, the receiving plate 65 having a curved surface and the linear member 66 are provided at the positions left at a predetermined distance from a region where the opening 12 of the test strip bottle 10 is moved by its turning on a shaft 56. Thus, even when the test strip bottle 10 faces downward, the holding portions 4 of the test strips 1 protrude a predetermined length from the opening 12, but the test strips 1 do not fully protrude from the test strip bottle 10.

Discrimination whether the air chuck 67 can adsorb the test strip 1 or not is carried out in two stages by a vacuum degree of air sucked from the suction holes 69. In the first stage, when two of the test strips 1 are adsorbed or the test strip 1 is adsorbed obliquely, it is estimated that two of the suction holes 69 of the air chuck 67 are not blocked completely, so that discrimination is carried out with a low level of a vacuum degree. In the second stage, discrimination is carried out with a high level of a vacuum degree after the flappers 78 are closed and the test strip 1 is aligned in parallel to the air chuck 67. The discrimination level is set to an optimum value at the time of initializing operation by measuring the vacuum degree obtained by a vacuum pump and the vacuum degree under a state that the suction holes 69 of the air chuck 67 are open.

The test strip 1 obliquely adsorbed to the air chuck 67 is aligned in parallel to the air chuck 67 by closing the flappers 78. In the case where two or more of the test strips 1 are obliquely superposed and adsorbed to the air chuck 67, when the flappers 78 are closed, excess test strips 1 other than the test strip 1 adsorbed to the adsorbing surface of the air chuck 67 are not adsorbed to the air chuck 67, so that the excess test strips 1 are dropped into the test strip bottle 10 and only one test strip 1 is drawn out.

When the test strip bottle 10 is turned on the shaft 56, the O-ring 63 mounted on the entire peripheral portion of the bottom of the bottle holder 50 is contacted with the turning auxiliary plate 64 to make the test strip bottle 10 turn on its axis. By turning the test strip bottle 10 on its axis, the test strips 1 are stirred and moved to be aligned in parallel to the central axis of the test strip bottle 10, so that they are easily adsorbed to the air chuck 67.

EXAMPLES

One embodiment of the test strip pick-up mechanism in an automated analyzer of the present invention is described in detail by referring to the drawings. As shown in FIG. 1 to FIG. 8, the tubular test strip bottle 10 is a test strip containing bottle containing a plurality of the test strips (not shown) with the holding portions facing to the opening 12 and the desiccant 11, such as molecular sieves, from which the desiccant 11 and a lid are removed. The test strip bottle 10 is formed such that its depth is slightly longer than the length of the test strips and its diameter is smaller than the length of the test strips. The desiccant 11 is removed from the test strip bottle 10 and disposed at a pocket 9 where it dehumidifies the chamber 13.

The test strip bottle 10 at the side of the opening 12 is not engaged to the inner part 22 of the bottle holder 14, but engaged to about a half position thereof and is removably held by a pressing member 16 provided at a gap between peripheral wall pieces 15. The bottom of the test strip bottle 10 engaged with the bottle holder 14 is lifted up about 5 to 10° from a horizontal plane. A bottle guide 17 is mounted on the peripheral wall piece 15 below the bottle holder 14 such that the test strip bottle 10 is easily engaged with the bottle holder 14.

A bottle keeper 18 is mounted on the bottle guide 17 such that when the test strip bottle 10 is engaged with the bottle holder 14, the bottle keeper 18 is contacted with the bottom of the test strip bottle 10, and an engagement state can be confirmed visually with naked eyes. At the upper portion of the bottle holder 14 between the opening 12 of the test strip bottle 10 and the inner part 22, the groove 19 pierced into the inner portion of the test strip bottle 10 is formed in the peripheral direction. The claws 21 mounted on the frame 20 such that they are movable on the axis are pressed to the peripheral surface of the test strip bottle 10 by springs not shown in the figures, and enter into and are engaged with the groove 19 by reciprocative turning of the bottle holder 14 on its axis.

The long guide member 23 is extended from the inner part 22 in parallel to the central axis of the test strip bottle 10. The guide member 23 has the guide portion 24 which is shorter than the depth of the test strip bottle 10 and has a L-shaped notch over the entire length. At the upper portion of the bottle holder 14, the test strip pick-up portion 25 connected to the groove 19 is formed in the longitudinal direction. The width of the test strip pick-up portion 25 is formed to be slightly larger than the width of a test strip.

The peripheral surface of the guide member 23 is a curved surface such that the test strip bottle 10 is engaged at a gap between the peripheral wall pieces 15 of the bottle holder 14. The suction holes 26 are formed on the guide portion 24 which is adjacent to the test strip pick-up portion 25, communicate with suction holes formed on the bottle holder 14 and a worm gear 27 and further are connected to a vacuum pump not shown in the figures.

The bottle holder 14 is connected to the bottle turning motor 32 via a power transmission member comprising the worm gear 27, a worm 30, a belt 31 and a pulley 46. A frame 33 is mounted on the bottle holder 14 via a bearing 48. One end of a shaft 34 disposed on the same axis of the worm 30 is mounted on the frame 33, and the other end of the shaft 34 is connected to a motor 36 via a gear 35 and a gear 47.

The air chuck 28 has the suction holes 37 connected a vacuum pump not shown in the figures via a suction tube 38. The air chuck 28 is mounted on the movable member 39 such that the air chuck 28 is movable upward and downward, and forced upward by a spring 95. The width of the adsorbing portion of the air chuck 28 is substantially the same as the width of the test strips. The movable member 39 is engaged with the guide bar 40 having a threaded portion. One end of the guide bar 40 is connected to the test strip drawing out motor 41 such that the movable member 39 is movable in the right and left directions.

Above the air chuck 28, two of the air chuck depressing arms 42 are mounted on the shaft 44 which is connected to the air chuck depressing motor 43. One depressing arm 42 is disposed above the position at which a test strip is sucked and drawn out from the test strip bottle 10, and the other depressing arm 42 is disposed above the position at which the test strip is supplied to a transportation stage 45. A flag 49 is mounted on the lower end of the movable member 39, and limit switches 90 and 91 restricting the movement range of the movable member 39 are mounted on the wall of the chamber 13.

Another embodiment of the test strip pick-up mechanism of the present invention is described in detail. As shown in FIG. 9 to FIG. 12, the bottom side of the test strip bottle 10 is engaged with the bottle holder 50, and the test strip bottle 10 is removably held by a pressing member 52 provided at a gap between peripheral wall pieces 51. The bottle holder 50 is mounted on one end of a L-shaped holder arm 54 via a shaft 53 and turnable on the shaft 53. The other end of the holder arm 54 is connected to the shaft 56 of a gear wheel 55.

A pinion 57 engaged with the gear wheel 55 is connected to the shaft of the bottle turning motor 58. Flags 59 and 60 are mounted on the holder arm 54, and limit switches 61 and 62, restricting the turning range of the bottle holder 50, are mounted on the wall of the chamber 13. The O-ring 63 is mounted on the entire peripheral portion of the bottom of the bottle holder 50, and the turning auxiliary plate 64 which is contacted with the O-ring 63 is mounted below the bottle holder 50. Below the bottle holder 50, the receiving plate 65 having a curved surface and the linear member 66 are provided at the positions left at a predetermined distance from a region where the opening 12 is moved by turning the test strip bottle 10.

The air chuck 67 has the suction holes 69 connected to a vacuum pump not shown in the figures via a suction tube 68. The width of the test strip adsorbing portion of the air chuck 67 is substantially the same as the width of the test strips. The upper end of an arm portion 70 of the air chuck 67 is mounted on a slider 71. A slider 72 is disposed above the slider 71 and connected to the slider 71 by a spring 73. The sliders 71 and 72 are pierced by shafts 74 and 75 extended in the vertical direction, forced upward by a spring 85 and movable upward and downward.

One end of the shaft 74 is fixed to the movable member 76, and the other end thereof is fixed to a flapper holding member 77. One end of the shaft 75 is slidably mounted on the movable member 76, and the other end thereof is connected to the flappers 78 mounted on the flapper holding member 77. The slider 72 has a mechanical stopper not shown in the figures which determines the uppermost point, so that it does not move above the position shown in FIG. 10. However, the slider 72 is movable further upward, and when the slider 72 moves further upward, the shaft 75 is lifted up to close the flappers 78. A flag 92 is mounted on the lower end of the movable member 76, and limit switches 91 and 93 restricting the movement range of the movable member 76 are mounted on the walls of the chamber 13.

The flappers 78 are disposed at the both sides of the test strip adsorbing portion of the air chuck 67 such that the test strip adsorbed to the air chuck 67 is aligned in parallel. The movable member 76 is engaged with the guide bar 79 having a threaded portion, and one end of the guide bar 79 is connected to the test strip drawing out motor 84. The slider 71 has a rack 81. The rack 81 is engaged with a gear 82 mounted on the movable member 76. The shaft 83 is connected to the air chuck depressing motor 80 via gears 86 and 87, pierces the movable member 76 and has a groove not shown in the figures, being formed in the entire longitudinal direction. A gear 82 has a needle roller not shown in the figure, which rolls in the groove.

In the following, operations of picking up a test strip from a test strip bottle by using the test strip pick-up mechanism of the present invention is described.

Figure 13:
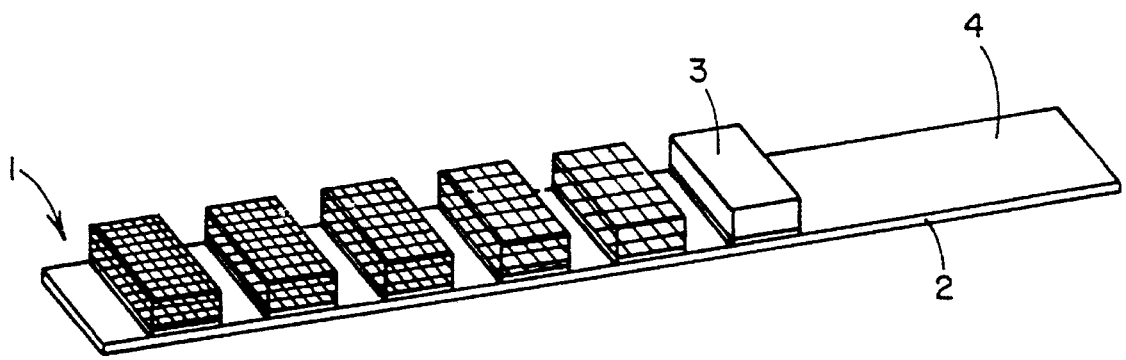
FIG. 13 is a perspective view of a test strip.

First, the lid is removed from the test strip containing bottle containing the test strips such that the holding portions 4 (see FIG. 13) face to the side of the opening 12. The door of the chamber 13 is opened, and the desiccant 11 is picked up from the test strip containing bottle and disposed at the pocket 9 in the chamber 13.

Next, in the case of the test strip pick-up mechanism shown in FIG. 1 to FIG. 8, the opening 12 (see FIG. 9) side of the test strip bottle 10 is engaged with the bottle holder 14. When the test strip bottle 10 is engaged with the bottle holder 14, the test strip bottle 10 is once lifted up to Position A in FIG. 2, and the bottom of the test strip bottle 10 is lifted up about 5 to 10° from a horizontal plane. Thus, the holding portions of the test strips (not shown) are protruded from the opening 12 to reach the inner part 22 of the bottle holder 14. Then, the bottle holder 14 is reciprocatively turned on its axis once or several times clockwise and counterclockwise by actuating the bottle turning motor 32.

That is, by reciprocatively turning the bottle holder 14 on its axis, the test strips are moved in the direction substantially orthogonal to its longitudinal direction, and the test strips are slid into the guide portion 24. These test strips are pushed into the guide portion 24 by the claws 21. When two or more of the test strips are slid into the guide portion 24, by pushing the test strip into the guide portion 24 and scraping out excess test strips by the claws 21 and reciprocatively turning the test strip bottle 10 on its axis, the excess test strips are thrown off, and only one test strip is adsorbed to the guide portion 24. When the test strip is not held by the guide portion 24, the above operations are repeated.

Then, the movable member 39 is moved by actuating the test strip drawing out motor 41, and the air chuck 28 enters into the test strip pick-up portion 25. Then, the air chuck 28 is pushed downward by the depressing arms 42 by actuating the air chuck depressing motor 43. Then, the test strip is drawn out from the test strip bottle 10 by being adsorbed to the air chuck 28, and the test strip is transported to the transportation stage 45. Thereafter, adsorption of the test strip is stopped, and the test strip is disposed on the transportation stage 45.

Discrimination whether the test strip is adsorbed to the air chuck 28 or not is carried out by measuring a vacuum degree of air sucked from the suction holes 37. When the test strip is drawn out from the test strip bottle 10, the bottle holder 14 is made start to turn on its axis by actuating the bottle turning motor 32, followed by the operations of picking up a next test strip. After the test strip pick-up operations are repeated several times, the bottom of the test strip bottle 10 is lifted up about 40° (Position A in FIG. 2) by actuating the motor 32, and a test strip in the test strip bottle 10 is moved to the inner part 22 side of the bottle holder 14.

In the following, test strip pick-up operations of the test strip pick-up mechanism shown in FIG. 9 to FIG. 12 are described. After the bottom side of the test strip bottle 10 is engaged with the bottle holder 50 from the obliquely upper direction (Position A in FIG. 10), the test strip bottle 10 is turned on the shaft 56 by actuating the bottle turning motor 58. The O-ring 63 is contacted with the turning auxiliary plate 64 mounted on the bottom of the chamber 13 below the bottle holder 50, and the test strip bottle 10 is reciprocatively turned on the shaft 53. By the reciprocative turning, the test strips inside the test strip bottle 10 are stirred and moved inside the bottle.

When the test strip bottle 10 is turned on the shaft 56 and the opening 12 faces in the obliquely lower direction, the holding portions 4 of the test strips (not shown) are protruded from the opening 12. However, the test strips are not fully protruded from the test strip bottle 10 by the receiving plate 65 and the linear member 66. When the opening 12 reaches a position facing in the obliquely lower direction of about 45°. (Position B in FIG. 10), turning of the bottle turning motor 58 is stopped by the flag 59 and the limit switch 61, and then the test strip bottle 10 is turned in a reverse direction by actuating the bottle turning motor 58.

The motor 58 is stopped at a position where the test strip bottle 10 is held in a horizontal state. At this time, the holding portions of the test strips protrude a predetermined length from the opening 12.

Then, after the air chuck 67 is transported to the position of the holding portions of the test strips protruding from the opening 12 by actuating the test strip drawing out motor 84, the motor 84 is stopped. The position of the test strips in the test strip bottle 10 is changed depending on the number of remaining test strips and the kind of test strips, so that the position of the air chuck 67 may be changed in response thereto. Then, the air chuck 67 is depressed by actuating the air chuck depressing motor 80. After a test strip is adsorbed, the motor 80 is turned in reverse to elevate the air chuck 67 to the original position. The motor 80 is further turned to close the flappers 78, and the test strip is aligned in parallel to the air chuck 67. Then, the motor 80 is turned in a positive direction to open the flappers 78.

Next, after the test strip is transported to the transportation stage 45 by actuating the test strip drawing out motor 84, adsorption of the test strip is stopped, and the test strip is disposed on the transportation stage 45. When the test strip is picked up from the test strip bottle 10, the test strip bottle 10 is reciprocatively turned on its axis to a position where the opening 12 faces in the obliquely lower direction of about 45° by actuating the bottle turning motor 58, followed by the operations of picking up a next test strip. By repeating the above operations, the test strips can be picked up continuously and automatically.

After the test strip pick-up operations described above are repeated several times, the test strip bottle 10 is turned on the shaft 56 by actuating the bottle turning motor 58, and by contact of the O-ring 63 with the turning auxiliary plate 64, the test strip bottle 10 is turned on its axis to stir and move the test strips in the test strip bottle 10. When the test strip bottle 10 is transported to the position at which the test strip bottle 10 is firstly set (Position A in FIG. 10), the motor 58 is stopped by the flag 60 and the limit switch 62.

The present invention is not limited to the above embodiments and can be applied to the case that a commercially available test strip bottle is not set as such in an analyzer and test strips are placed in a larger-sized container which can contain a plurality of smaller-sized test strip bottles containing test strips.

According to the present invention, test strips can securely be supplied one by one by preventing two test strips from being picked up, and the probability of picking up a test strip can be enhanced, so that test strips can automatically be supplied smoothly. For example, when a test strip bottle containing a plurality of commercially available test strips is set as such in an analyzer, the test strips can directly be picked up from the test strip bottle without providing any specially designed test strips for the analyzer.

We claim:

1. A test strip pick-up mechanism in an automated analyzer, which comprises:

a bottle holder removably holding a test strip bottle containing a plurality of test strips and having a pierced groove formed in a peripheral direction and a test strip pick-up portion connected to the groove and formed in a longitudinal direction;

a bottle turning motor connected to the bottle holder;

a guide member extended from an inner part of the bottle holder in parallel to a central axis of the test strip bottle and having a L-shaped guide portion formed over an entire length of the guide member with suction holes for adsorbing the test strips being formed on the guide portion which is adjacent to the test strip pick-up portion;

claws engaged with the groove of the bottle holder;

an air chuck having suction holes for drawing out the test strips contained in the test strip bottle;

a movable member on which the air chuck is mounted;

a test strip drawing out motor connected to the movable member via a guide bar;

depressing arms for pushing the air chuck downward; and an air chuck depressing motor connected to the depressing arms via a shaft.

2. A test strip pick-up mechanism in an automated analyzer, which comprises:

a bottle holder removably holding a test strip bottle containing a plurality of test strips;

a bottle turning motor connected to the bottle holder;

an O-ring mounted on an entire peripheral portion of the bottom of the bottle holder;

a turning auxiliary plate which is contacted with the O-ring and makes the bottle holder turn on its axis;

an air chuck having suction holes for drawing out the test strips contained in the test strip bottle;

a movable member on which the air chuck is mounted such that the air chuck is movable upward and downward;

a test strip drawing out motor connected to the movable member via a guide bar;

an air chuck depressing motor connected to the air chuck via a shaft;

flappers disposed at both sides of the test strip adsorbing portion of the air chuck, which open and close accompanied with upward and downward movements of the air chuck; and a receiving plate having a curved surface and a linear member both of which are provided at positions left from a region where an opening is moved by turning the test strip bottle.

* * * * *